(12) United States Patent
Tanifuji et al.

(10) Patent No.: US 7,370,967 B2
(45) Date of Patent: May 13, 2008

(54) METHOD AND APPARATUS FOR OPTICAL IMAGING OF RETINAL FUNCTION (75) Inventors: Manabu Tanifuji, Saitama (JP); Kazushige Tsunoda, Saitama (JP)

(73) Assignee: Riken, Saitama (JP)

( * ) Notice: Subject to any disclaimer, the term of this patent is extended or adjusted under 35 U.S.C. 154(b) by 75 days.

(21) Appl. No.: 10/598,207

(22) PCT Filed: Jan. 24, 2005

(86) PCT No.: PCT/JP2005/000836

§ 371 (c)(1), (2), (4) Date: Aug. 21, 2006

(87) PCT Pub. No.: WO2005/084526

PCT Pub. Date: Sep. 15, 2005

(65) Prior Publication Data

US 2007/0139613 A1 Jun. 21, 2007

(30) Foreign Application Priority Data

Feb. 20, 2004 (JP) ............................. 2004-044055

(51) Int. Cl.
*A61B 3/14* (2006.01)

(52) U.S. Cl. ..................... 351/206; 351/213; 351/221

(58) Field of Classification Search ................ 351/205, 351/206, 210, 213, 221, 246
See application file for complete search history.

(56) References Cited

U.S. PATENT DOCUMENTS 6,478,424 B1 * 11/2002 Grinvald et al. ............ 351/206
7,118,217 B2 * 10/2006 Kardon et al. .............. 351/206

FOREIGN PATENT DOCUMENTS

| JP | 1-300923 | 12/1989 |
|----|----------|---------|
| JP | 04-327831 | 11/1992 |
| JP | 2000-504256 | 4/2000 |
| JP | 2002-521115 | 7/2002 |
| JP | 2002-543863 | 12/2002 |

* cited by examiner

*Primary Examiner*—Huy K Mai
(74) *Attorney, Agent, or Firm*—Griffin & Szipl, P.C.

(57) ABSTRACT

A method for optical imaging of retinal function comprises an illuminating observing step (S1) of illuminating the retinal region (2) of the rear surface of an eyeball (1) including the macular area and the optic disk with an invisible light (3) and observing the retinal region (2), a stimulating step (S3) of illuminating the retinal region (2) with a visible flash light (4) to stimulate a retinal function including an optic disk's function, an imaging step (S2) of capturing images (A, B) before and after the stimulation of the retinal region (2) illuminated with the invisible light, and a calculating step (S4) of detecting the change of the retinal function of the retinal region from the images (A, B) before and after the stimulation. In the calculating step, the images (A, B) before and after the stimulation are registered in advance, and the change of the retinal function of the retinal region is displayed with an image from the registered images.

9 Claims, 11 Drawing Sheets

FIG.5A image A immediately before stimulation

FIG.5B 1.0mm image B after stimulation, the neuron cells are active

FIG.7A enlargement and reduction

FIG.7B rotation

FIG.7C translation

FIG.9A fundus photograph of retina
(center is macular area)

macular area

FIG.9B

FIG.9C
functional topography of macular area achieved by optical measurement

FIG.9D cross section of FIG.9C

FIG.10A  recorded area on retina recorded area
on retina (white line)

A: macular area
B: optic disk

FIG.10B   distribution of neural activity
by electroretinogram down
up 200 nV
0   80 mSec

FIG.10C correlation between intrinsic signal and
signal intensity mesured by electroretinogram intrinsic signal intensity
(chang of refrection rate:%)

correlation
coefficient
=0.83
(n=45)

local avtivity intensity of neurons
by electroretinogram

METHOD AND APPARATUS FOR OPTICAL IMAGING OF RETINAL FUNCTION

This is a National Phase Application in the United States of International patent application No. PCT/JP2005/000836 filed Jan. 24, 2005, which claims priority on Japanese Patent Application No. 044055/2004, filed Feb. 20, 2004. The entire disclosures of the above patent applications are hereby incorporated by reference.

BACKGROUND OF THE INVENTION

1. Technical Field of the Invention

The present invention relates to method and apparatus for optical imaging of retinal function.

2. Description of the Related Art

Currently there are known technologies such as fundus photography, fluorescein angiography, and optical coherent tomography(OCT) as general ophthalmic diagnostic imaging technologies.

The fundus photography is to image a part of the ocular fundus on an optical film or a CCD while illuminating the inside of a patient's eye through the pupil of the eye. Although it is effective to detect hemorrhage of an eye ground, retinal arteriosclerosis, or other abnormalities, it cannot detect the retinal function and the optic disk function.

The fluorescein angiography is to visualize a fluorescent labeling pattern of the microvascular network of the retina by injecting fluorescent agent. Although it is effective to detect defects of a retinal vasculature, it can acquire only indirect information about the retinal function and the optic disk function.

The OCT is to provide an image of the retinal section anatomically. Thus, it does not reflect any functional problem at all.

Therefore, the conventional general ophthalmic diagnostic imaging technologies have been incapable of directly detecting the functional structure of the retina to make use of it for diagnosis or the like.

On the other hand, it is already known that a change is detected in the reflected light intensity of an area where a neural activity arising from stimulation occurs when illuminating a neural tissue such as the cerebral cortex with a light having a certain wavelength. The change is referred to as "intrinsic signal." The "intrinsic signal" indicates an increase of the deoxyhemoglobin level of the blood arising from the neural activity, an increase in a blood flow or a blood volume, or the change in absorption of light caused by a structural change in the neural tissue.

Furthermore, there is known "an optical imaging method" of continuously recording a reflected light intensity by illuminating the neural tissue with a light having a certain wavelength as means for detecting the intrinsic signal. This optical imaging method facilitates the extraction of a two-dimensional functional structure, for example, referred to as an ocular dominance column of monkey primary visual cortex, by mapping the local activities of the neurons.

Moreover, Patent Document 1 discloses a technology for optical imaging the functional structure of the retina by applying the optical imaging method to the retina.

Figure 1:
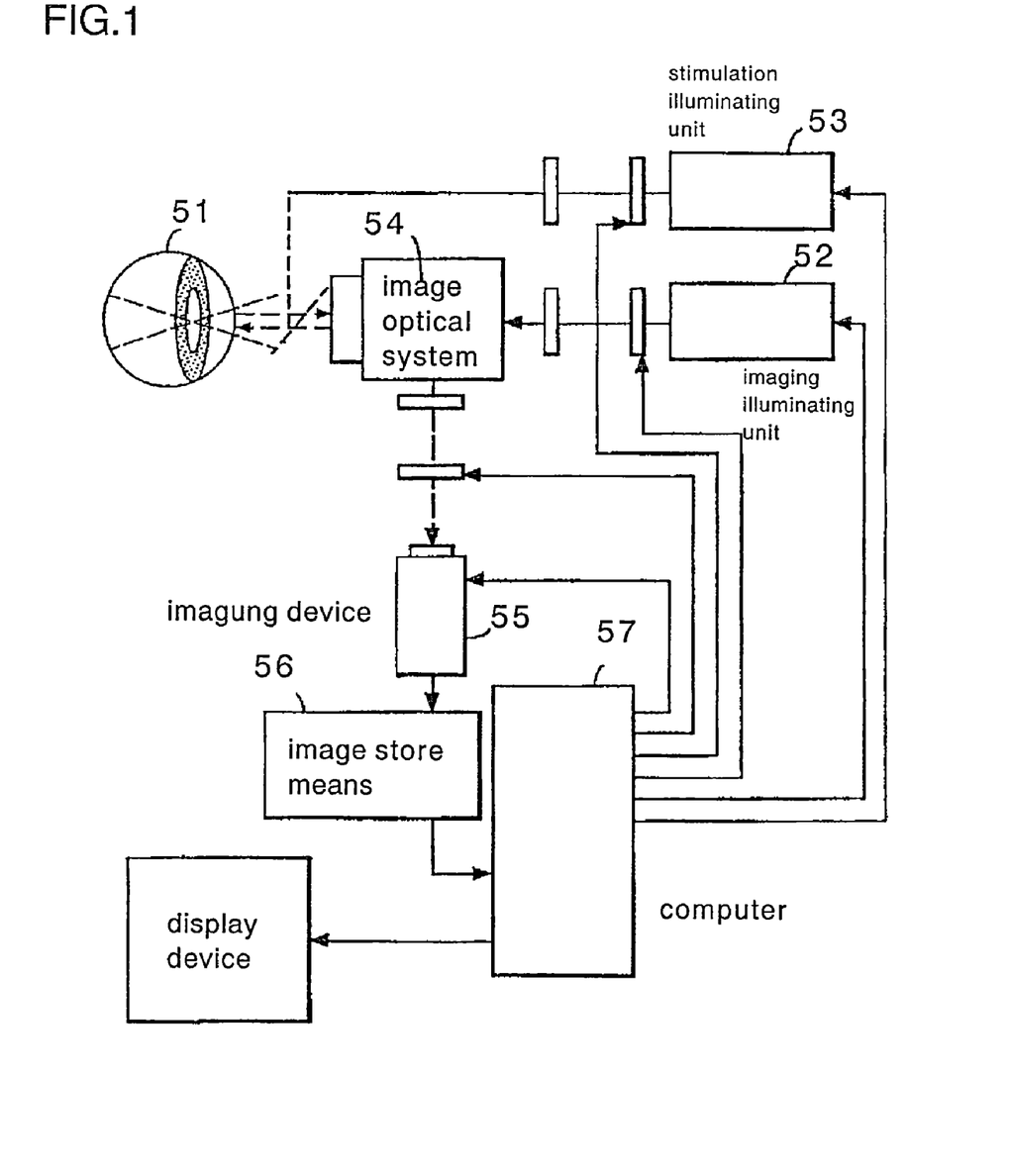
FIG. 1 is a schematic diagram of "the system and method for noninvasively imaging the retinal function" in the Patent Document 1.

"The system and method for noninvasively imaging the retinal function" in the Patent Document 1 relates to a system for imaging the change of reflectance of the retina and the intrinsic change caused by the retinal function. As shown in FIG. 1, the system includes an imaging illuminating unit 52 for illuminating retina 51, a retinal stimulation illuminating unit 53 for inducing a functional response, an imaging device 55 for receiving a light from the retina 51 via a retinal imaging optical system 54, image store means 56 for digitalizing and storing the image received from the imaging device 55, and a computer 57 for controlling the system operations and processing the stored image to output a differential function signal corresponding to the retinal function.

[Patent Document 1]

Japanese Unexamined PCT Publication No.2002-521115, "System and Method for Noninvasively Imaging Retinal Function"

The means of the above Patent Document 1 constantly illuminates the retina with a near infrared ray to calculate the change of brightness of a retinal image before and after illuminating the retina with a visible light that activates the neurons of the retina. The change of the intrinsic signal, however, is minute (for example, around 0.1%). Thus, to detect the change, there has been a need to give an examinee anesthesia or the like to fix his or her eyeball strictly during recording.

Therefore, when the above method is applied to a conscious examinee (for example, due to earlier diagnosis) without giving anesthesia or the like, it has been hard to detect a minute difference in the intrinsic signal very reliably because of slight movements of the examinee's eyeball that inevitably occur during recording. Moreover, particularly a patient having a disorder in the retina finds difficulty fixing. In this manner, the problem caused by the movements of an eyeball has been serious.

On the other hand, the human retina has a characteristic that the visual functions concentrate on "the macular area" located in the center where an image comes into a focus. Specifically, the macular area, where cone photoreceptors concentrate most intensively, is the most important area to maintain normal sight. Therefore, it is extremely important to image the function of the macular area and the optic disk in the clinical ophthalmology or the retinal physiology.

According to the means in the Patent Document 1 described above, the discoloration or change in hemoglobin caused by stimulation is relatively small. Therefore, it has a problem that it cannot detect the change of the intrinsic signal that genuinely reflects the photoreceptor function of the macular area.

SUMMARY OF THE INVENTION

The present invention has been provided to resolve the above problem. Specifically, a first object of the present invention is to provide method and apparatus for optical imaging of retinal function capable of detecting a minute difference in an intrinsic signal caused by the retinal function and the optic disk's function extremely reliably even if an examinee's eyeball is moving.

A second object of the present invention is to provide method and apparatus for optical imaging of retinal function capable of detecting the change of an intrinsic signal (the retinal function) in the macular area where the visual functions concentrate, in distinction from the influence of the discoloration or change in hemoglobin.

According to the present invention, there is provided a method for optical imaging of retinal function comprising: an illuminating observing step of illuminating the retinal region of the rear surface of an eyeball including the macular area and the optic disk with an invisible light and observing the retinal region; a stimulating step of illuminating the retinal region with a visible flash light to stimulate the retinal function including the optic disk's function; an imaging step of capturing images A, B before and after the stimulation of the retinal region illuminated with the invisible light; and a calculating step of detecting the change of the retinal function of the retinal region from the images A, B before and after the stimulation, wherein, in the calculating step, the images A, B before and after the stimulation are registered in advance, and the change of the retinal function is displayed with an image from the registered images.

Moreover, according to the present invention, there is provided an apparatus for optical imaging of retinal function comprising: a stimulator for illuminating the retinal region of the rear surface of an eyeball including the macular area with a visible flash light to stimulate the retinal function including the optic disk's function; an illuminator for illuminating the retinal region with an invisible light; an imaging device for capturing images A, B before and after the stimulation of the retinal region illuminated with the invisible light; and a calculator for detecting the change of the retinal function of the retinal region from the images A, B before and after the stimulation, wherein the calculator has an image processing program for registering the images A, B before and after the stimulation in advance and subsequently displaying the retinal function with an image from the registered images by using a computer.

According to the method and apparatus of the present invention, the images A, B before and after the stimulation are registered in advance by using the computer and subsequently the change of the retinal function including the optic disk's function is displayed with the image from the registered images. Therefore, even if there are movements in an examinee's eyeball, a minute difference in an intrinsic signal caused by the retinal function and the optic disk's function can be detected with high reliability.

Moreover, according to the preferred embodiment of the present invention, the retinal region of the rear surface of the eyeball including the macular area is stimulated by using a flash device for illuminating the retinal region with a visible flash light having a wavelength greater than or equal to 470 nm and less than or equal to 780 nm that the examinee gets stimulated in the form of a single or flickering light, and the images are captured continuously by using an infrared light emitting device for continuously emitting an infrared light having a wavelength greater than or equal to 800 nm and less than 1000 nm that the examinee cannot recognize almost at all and does not get stimulated. Therefore, it is possible to detect the change of the intrinsic signal (the retinal function) in the macular area where the visual functions concentrate, in distinction from the influence of the discoloration or change in hemoglobin.

Moreover, the apparatus of the present invention includes a fixation point forming device for forming a fixation point that can be fixed by the examinee on the retina.

This arrangement assists the examinee in fixation, which reduces the movements of the examinee's eyeball.

Furthermore, the apparatus of the present invention includes an optical filter for selectively dimming a reflected light from the vicinity of the optic disk to capture the images of the macular area without saturation.

This arrangement enables the correction of the image position with the feature points of a blood vessel in the macular area and in the vicinity thereof used as measures.

ADVANTAGES OF THE INVENTION

As described above, the method and the apparatus for optical imaging of retinal function according to the present invention have excellent such effects that they enable the detection of a minute difference in an intrinsic signal caused by the retinal function with high reliability and the detection of the change of the intrinsic signal (retinal function) in the macular area where the visual functions concentrate, in distinction from the influence of the discoloration or change in hemoglobin.

The optic disk is an area where the axons of the retinal ganglion cells concentrate. In the present invention, the retinal functions can be evaluated in more detail by imaging "the change of the reflectance to a light stimulation" in this area.

Other objects and advantages of the present invention will be apparent from the description given hereinafter with reference to the appended drawings.

DESCRIPTION OF THE PREFERRED EMBODIMENTS

The present invention will be described below with reference to the accompanying drawings. The same reference numerals have been applied to like parts in the drawings and their overlapped description is omitted here.

Figure 2:
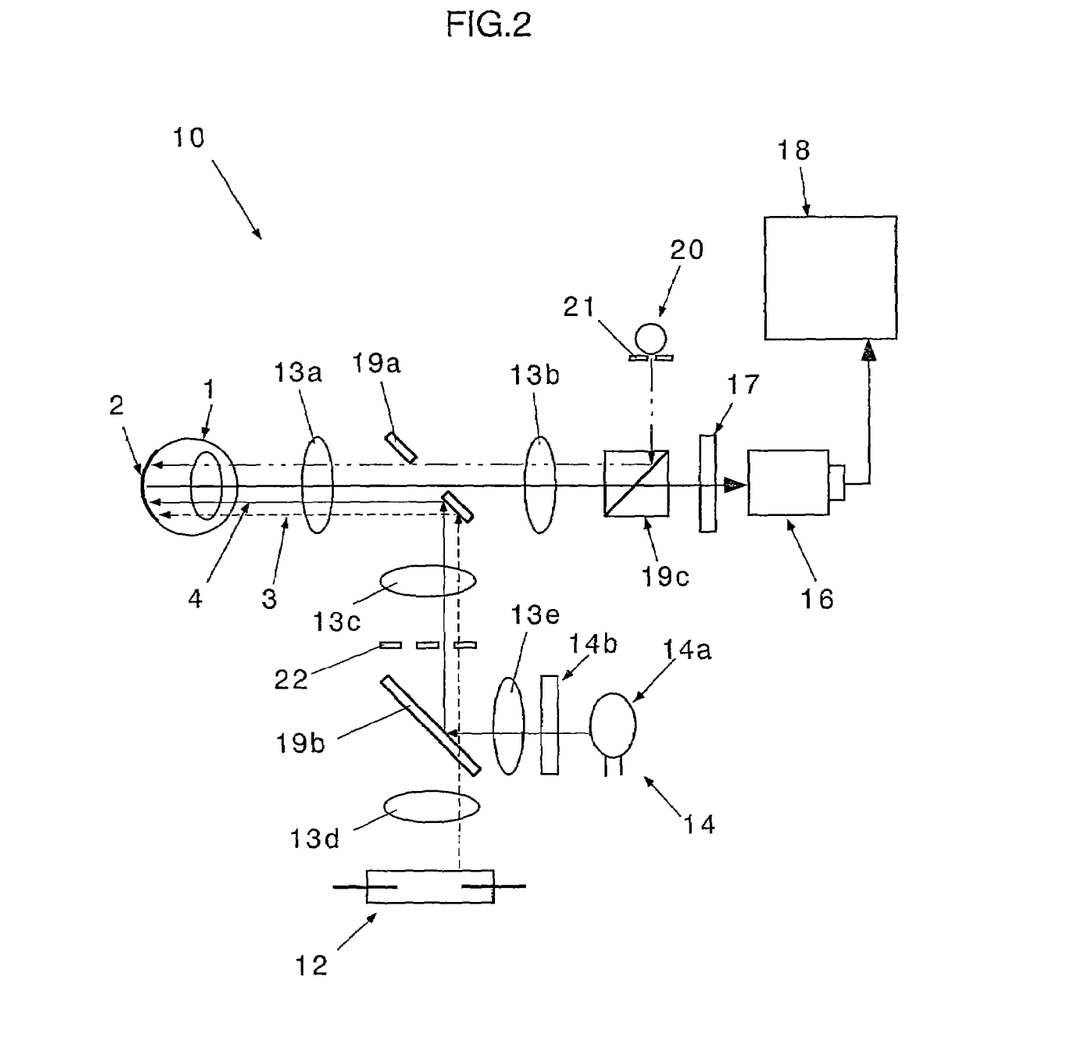
FIG. 2 is a general configuration diagram of an apparatus for optical imaging of retinal function according to the present invention.

Referring to FIG. 2, there is shown a general configuration diagram of an apparatus for optical imaging of retinal function according to the present invention.

The apparatus 10 for optical imaging of retinal function includes an illuminator 12, a stimulator 14, an imaging device 16, a calculator 18, and a fixation point forming device 20.

In this diagram, there are shown an objective lens 13a, an imaging lens 13b, a projection lens 13c, condenser lenses 13d and 13e, and half mirrors 19b and 19c.

Moreover, a reference numeral 19a indicates a perforated mirror having a fringe reflecting a ring-shaped illumination luminous flux and an aperture in its center for passing a photographing luminous flux. A reference numeral 21 indicates a pinhole plate having a small hole for forming a fixation point and preferably it is slidable for the purpose of guiding the macular area of the fundus. A reference numeral 22 indicates a ring slit plate, which is for use in forming the illumination luminous flux into a ring shape, includes a so-called doughnut-shaped opening whose center is shielded.

The illuminator 12 illuminates a retinal region 2 including an optic disk with an invisible light 3 for observation. The illuminator 12 is preferably an infrared light emitting device for continuously emitting an infrared light having a wavelength greater than or equal to 800 nm and less than 1000 nm. In this example, the illuminator 12 is a halogen lamp for emitting only an infrared light having a wavelength greater than or equal to 800 nm and less than 1000 nm. The invisible light 3 for observation emitted from the halogen lamp 12 passes through the half mirror 19b, reflects off the perforated mirror 19a, passes through the objective lens 13a, and is continuously applied to the retinal region 2 including the macular area and the optic disk via the lens of the eyeball 1.

The stimulator 14 illuminates the retinal region 2 of the rear surface of the eyeball 1 including the macular area and the optic disk with a visible flash light 4 for stimulation to stimulate the retinal function and the optic disk's function. The stimulator 14 includes a flash device 14a such as, for example, a Xe flash lamp and an interference filter 14b. The flash device 14a illuminates the visible flash light in the form of a single or flickering light. The interference filter 14b has a function of allowing only the visible light having a wavelength greater than or equal to 470 nm and less than or equal to 780 nm to pass through. In this example, the visible flash light 4 emitted from the flash device 14a passes through the interference filter 14b and reflects off the half mirror 19b and the perforated mirror 19a so as to follow the same optical path as the invisible light 3 and then it is applied for a short time to the retinal region 2 including the macular area via the lens of the eyeball 1.

The imaging device 16 captures images A, B before and after the stimulation of the retinal region 2 illuminated with the invisible light 3. The imaging device 16 is, for example, a CCD camera or a video camera. The images of the retinal region 2 illuminated with the invisible light 3 are continuously captured and stored by the imaging device 16 through the half mirror 19c. In addition, the imaging device 16 is preferably provided with an optical filter 17 for selectively dimming the reflected light from the vicinity of the optic disk to capture the images of the macular area without saturation, so that the image position can be corrected with the feature points of a blood vessel in the macular area and in the vicinity thereof used as measures.

The calculator 18 detects the change of the retinal function and the optic disk's function of the retinal region 2 from the captured images A, B before and after the stimulation. The calculator 18 has an image processing program for previously registering the images A, B before and after the stimulation and subsequently displaying the change of the retinal function and the optic disk's function of the retinal region with an image from the registered images by using a computer.

Moreover, the apparatus 10 for optical imaging of retinal function according to the present invention further includes the fixation point forming device 20 for forming a fixation point that can be fixed by an examinee on the retina. Preferably the fixation point forming device 20 is, for example, a laser light source or point light source of a less stimulating visible continuous light. In this example, the less stimulating light emitted from the fixation point forming device 20 passes through the pinhole plate 21, reflects off the half mirror 19c, and passes through the perforated mirror 19a so as to follow the same optical path as the invisible light 3. It then passes through the objective lens 13a and continuously comes into a focus on the retinal region 2 including the macular area and the optic disk via the lens of the eyeball 1 so as to assist the examinee in fixation, thereby reducing the movements of the examinee's eyeball.

Figure 3:
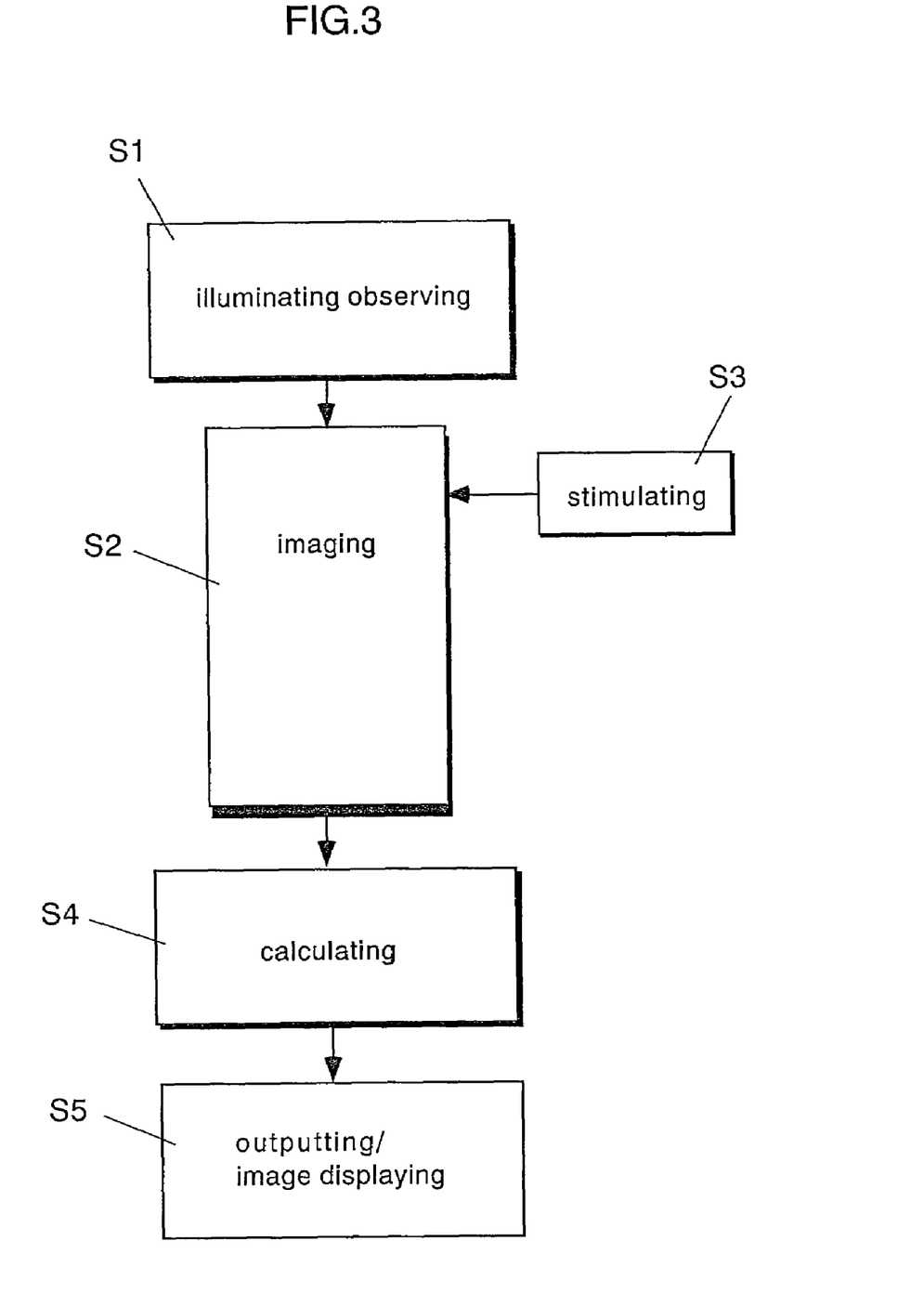
FIG. 3 is a flowchart showing a method of the present invention.

Referring to FIG. 3, there is shown a flowchart of a method of the present invention.

As shown in this diagram, the method of the present invention includes an illuminating observing step S1, an imaging step S2, a stimulating step S3, a calculating step S4, and an outputting (image displaying) step S5.

In the illuminating observing step S1, the retinal region 2 of the rear surface of the eyeball 1 including the macular area and the optic disk is illuminated with the invisible light 3 for observation. The invisible light 3 for observation is a continuous infrared light having a wavelength greater than or equal to 800 nm and less than 1000 nm. Preferably the illuminating observing step S1 continues until the completion of capturing all images.

In the imaging step S2, the images A, B of the retinal region 2 illuminated with the invisible light 3 are captured before and after the stimulation with the visible flash light 4. This imaging step S2 is performed before and after the stimulating step S3. Particularly after the stimulating step, it is preferable that the plurality of images are continuously captured.

In the stimulating step S3, the retinal region 2 of the rear surface of the eyeball 1 including the macular area and the optic disk is illuminated with a visible flash light 4 for stimulation to stimulate the retinal function and the optic disk's function. The visible flash light is a single or flickering light having a wavelength greater than or equal to 470 nm and less than or equal to 780 nm.

In the calculating step S4, the change of the retinal function and the optic disk's function is detected from the images A, B before and after the stimulation.

In the calculating step S4, the images A, B before and after the stimulation are registered in advance and subsequently the change of the retinal function and the optic disk's function is displayed with an image from the registered images.

Furthermore, in this registering, the image B after the stimulation is subjected to translation, rotation, enlargement or any other linear operation or nonlinear image transformation, and then the image B subjected to the linear operation or image transformation is compared with the image A by using an appropriate evaluation function to acquire an optimal image B' registered to the image A.

Figure 4A:
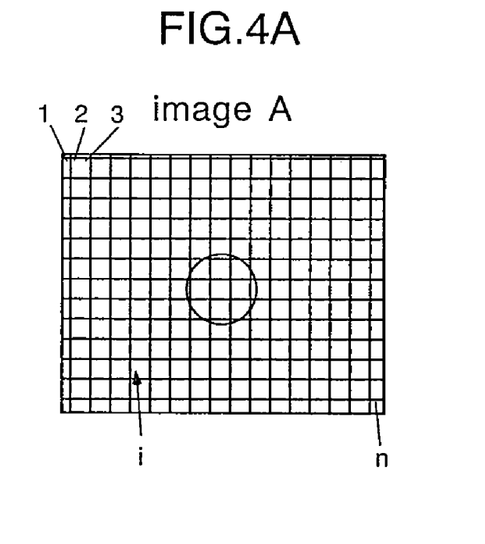
FIG. 4A is a diagram schematically showing a method of an image before the stimulation.
Figure 4B:
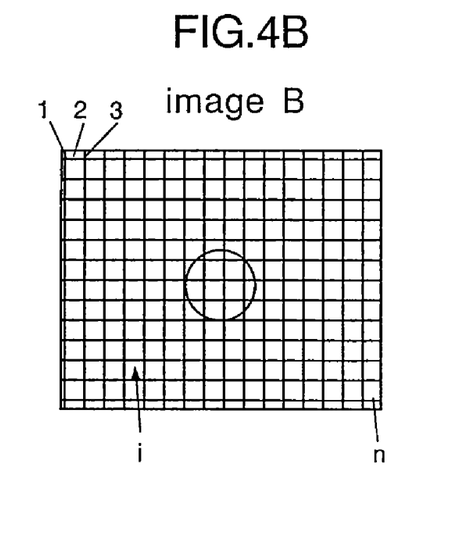
FIG. 4B is a diagram schematically showing an image after the stimulation.

Referring to FIG. 4, there is shown a diagram typically illustrating the method of registering the images A, B before and after the stimulation. In this diagram, FIG. 4A shows the image A before the stimulation captured by a CCD camera or a video camera, having 1024×768 pixels, for example. The pixels are assumed sequentially as 1, 2, 3, - - - i, - - - n and the pixel values (brightness in this example) of the pixels are assumed as $x_i$ ($i=1, 2, 3, $ - - - $i, $ - - - $n$). Similarly, FIG. 4B shows the image B after the stimulation. The pixels are assumed sequentially as 1, 2, 3, - - - i, - - - n and the pixel values of the pixels are assumed as yi (i=1, 2, 3, - - - i, - - - n).

The average of the brightness of the image A or image B is indicated by an overlined x or y.

Figure 4C:
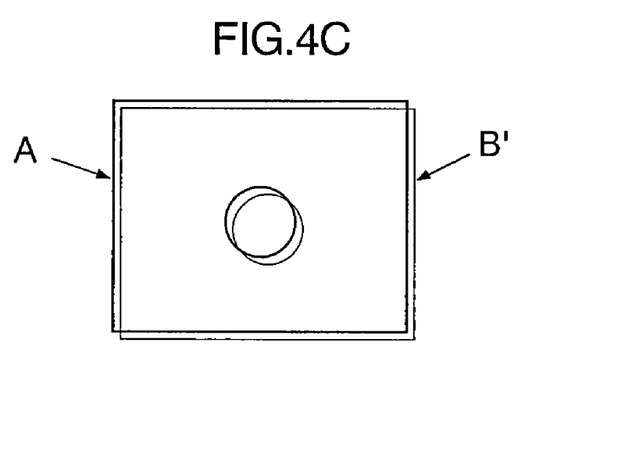
FIG. 4C is a diagram schematically showing a method of registering the images.

As shown in FIG. 4C, the registering is performed by obtaining an image B' by performing a linear operation or image transformation such as translation, rotation, enlargement or any other linear operation or nonlinear image transformation on the image B and calculating a correlation coefficient γ between the overlapping regions of the two images A and B' or between the corresponding pixel values xi and yi (i is a positive integer of n) of the feature points by using an expression (1) of [Eq. 2] in order to achieve a transformation that provides the correlation coefficient closest to 1.

If two images are identical, the numerator matches the denominator and therefore γ=1. The more differences there are between them, the less or greater than 1γ is. While moving the image B' inch by inch relative to the image B, the correlation coefficient γ to the image A is acquired every time the image B' moves. The position is corrected according to the shift where the maximum correlation coefficient γ occurs. Thereafter, the difference between them is calculated.

[Eq. 2]

$$r = \frac{\sum (x_i - \bar{x})(y_i - \bar{y})}{\sqrt{\sum (x_i - \bar{x})^2} \sqrt{\sum (y_i - \bar{y})^2}} \quad (1)$$

The registering method of the present invention is not limited to the above method, but any other known method may be used.

The image display is performed in step S5 shown in FIG. 3 by calculating a fraction a/b where a and b are the brightness of the image A and the brightness of the image B', respectively, or the difference between them Δ=a−b for each corresponding pixel from the image A before the stimulation and the optimal registered image B' after the stimulation and associating the fraction or the difference with the pixel position on the display.

According to the method and the apparatus of the present invention described above, the images A and B before and after the stimulation are registered in advance and subsequently the change of the retinal function is displayed with the image from the registered images by using the computer. Therefore, even if there are movements in an examinee's eyeball, a minute difference in the intrinsic signal caused by the retinal function and the optic disk's function can be detected with high reliability.

Moreover, the retinal region of the rear surface of the eyeball including the macular area and the optic disk is stimulated by using the flash device for illuminating the retinal region with a visible flash light having a wavelength greater than or equal to 470 nm and less than or equal to 780 nm in the form of a single or flickering light, and the images are continuously captured by using the infrared light emitting device for continuously emitting an infrared light having a wavelength greater than or equal to 800 nm and less than 1000 nm. Therefore, it is possible to detect the change of the intrinsic signal (the retinal function) and the optic disk's function, in distinction from the influence of the discoloration or change in hemoglobin other than those indicated by the intrinsic signal.

Moreover, the optic disk is an area where the axons of the retinal ganglion cells concentrate. In the present invention, the retinal functions can be evaluated in more detail by imaging "the change of the reflectance to a light stimulation" in this area.

Hereinafter, preferred embodiments of the present invention will now be described.

In the visualization mechanism of neural activities, the stimulation of the retina by a visible light causes the activities of the neurons, which varies the oxygen consumption and the fine structure of tissue and thus induces the change of reflection intensity of an observed near infrared light (change of light scattering intensity).

The conventionally suggested signal detection method (the Patent Document 1) includes the steps of capturing the retinal image A immediately before the stimulation, capturing the retinal image B after the stimulation (during the activities of cells), and calculating the reflectance by dividing the retinal image A by the retinal image B or by subtracting the retinal image B from the retinal image A.

This change, however, is very subtle, which is of the order of 0.1% at most in terms of the change in brightness. Therefore, to detect the subtle signal from the conscious examinee with a high reliability, minute movements of the examinee's eye during recording becomes a serious problem.

First Embodiment

Figure 5A:
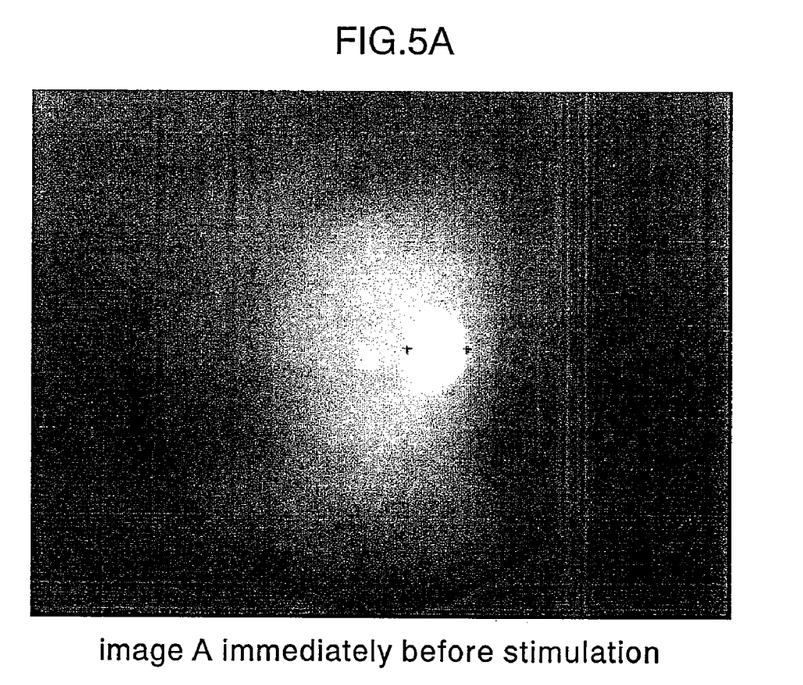
FIG. 5A is a diagram showing the image before the stimulation.
Figure 5B:
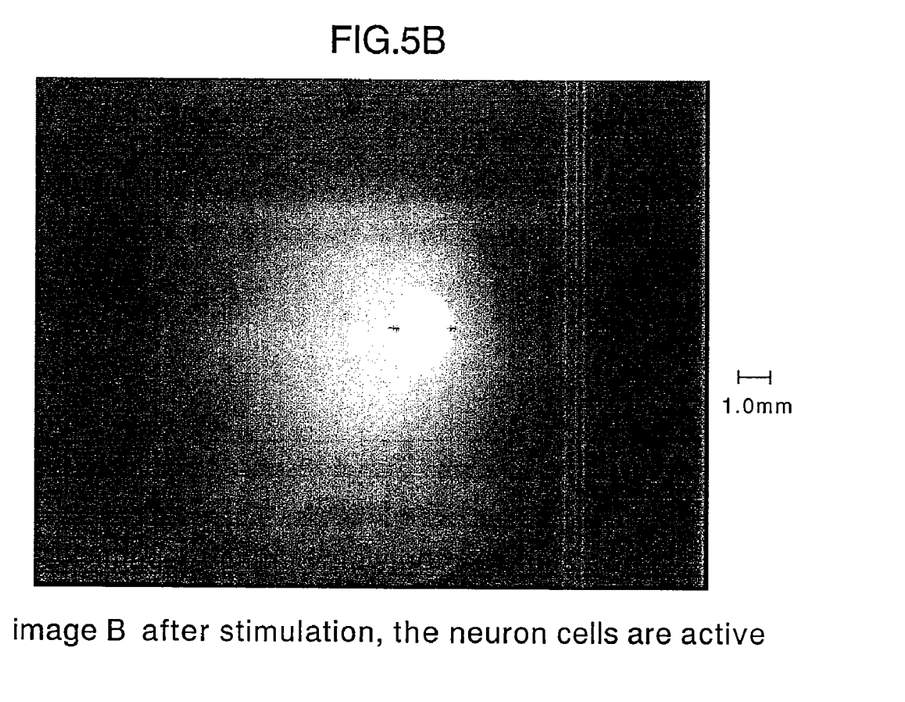
FIG. 5B is a diagram showing the image after the stimulation.

Referring to FIGS. 5A and 5B, there are shown the images before and after the stimulation. The image B (FIG. 5B) after the stimulation, in which the neurons are active, shifts relative to the image A (FIG. 5A) immediately before the stimulation to the extent that it is unrecognizable with eyes (in this embodiment, 0.1 to 0.2 mm).

Figure 6A:
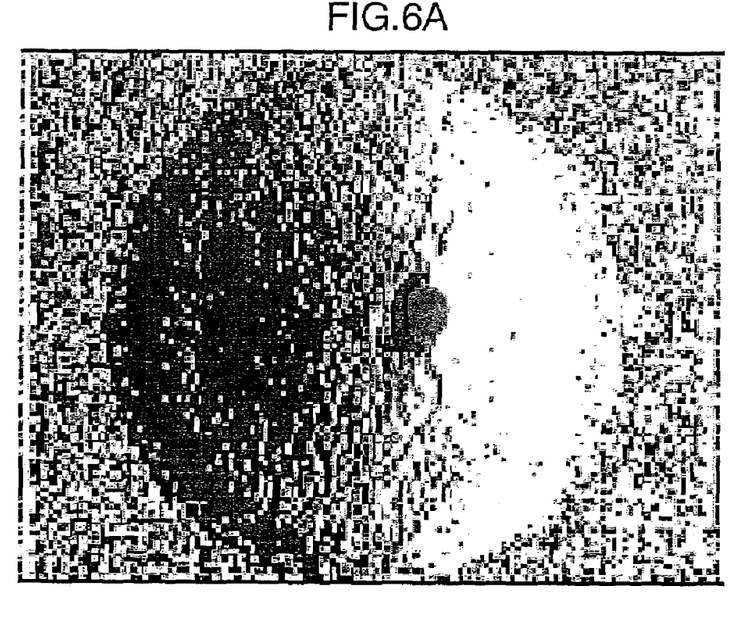
FIGS. 6A and 6B are diagrams each showing a first embodiment of the change of the retinal function and the optic disk's function according to the present invention or to a conventional example.

FIGS. 6A and 6B each show a first embodiment of the change of the retinal function and the optic disk's function according to the present invention or to the conventional example. The result (FIG. 6A) of dividing the retinal image B where the neurons are active by the retinal image A immediately before the stimulation according to the conventional method does not match a known typical activity pattern of the neurons of the retina, because the image B (FIG. 5B) where the neurons are active slightly shifts to the right relative to the image A (FIG. 5A) immediately before the stimulation.

Figure 6B:
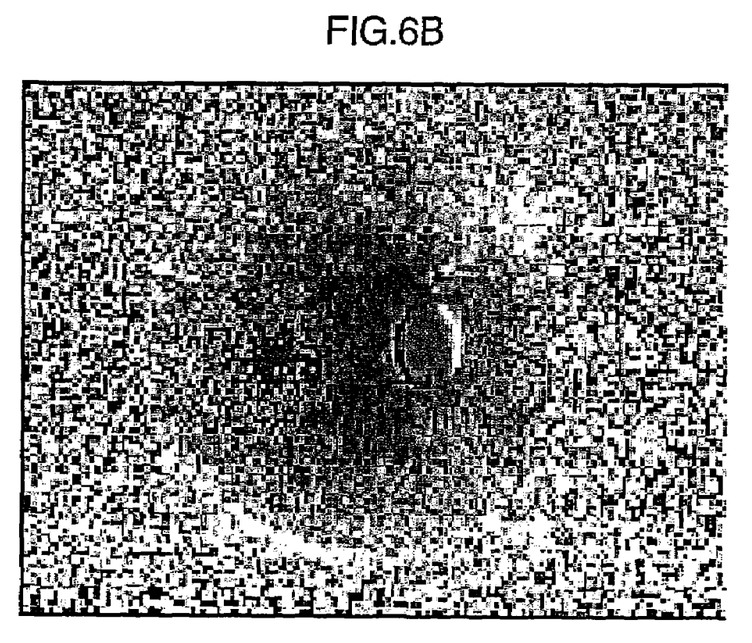

On the other hand, according to the method of the present invention, the anticipated (known) activity pattern of the neurons cells of the retina has been achieved by previously correcting the shift of the image, as shown by the result (FIG. 6B) of dividing the retinal image B where the neurons are active by the retinal image A immediately before the stimulation.

Figure 7A:
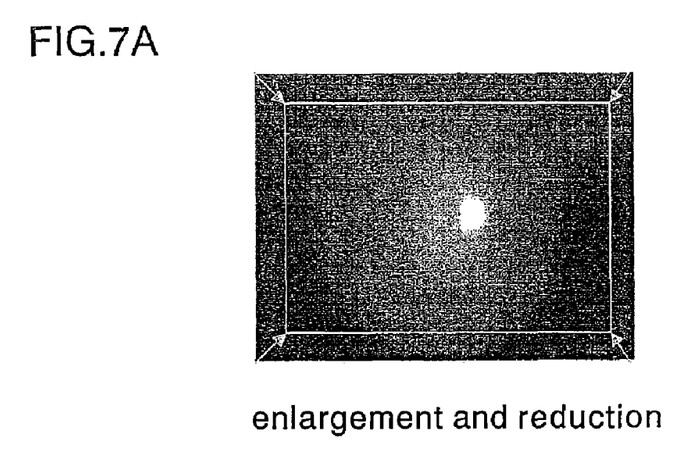
FIGS. 7A, 7B, and 7C are schematic diagrams each showing a registering method according to the present invention.
Figure 7B:
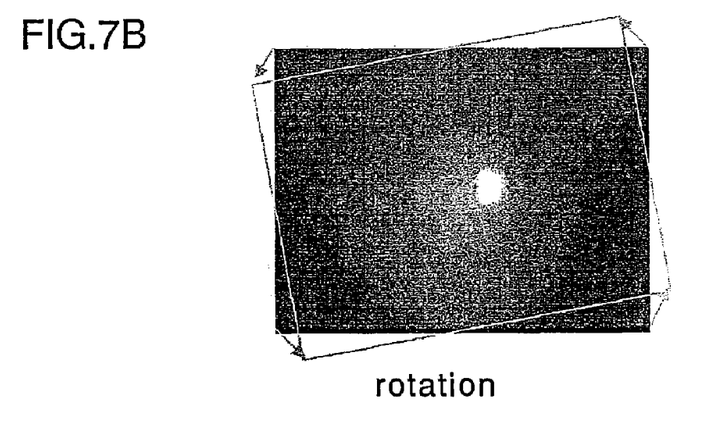
Figure 7C:
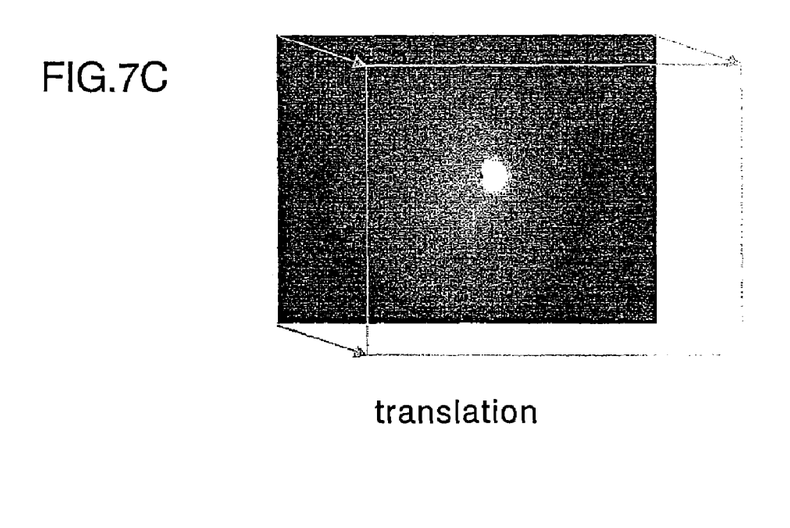

Referring to FIG. 7, there is shown a schematic diagram illustrating the registering method according to the present invention. In the method of the present invention, before doing the division of the images, the images A and B are matched with each other by performing linear operation such as translation, rotation, or enlargement, or nonlinear image transformation on the image B in such a way that the image B after the stimulation is matched with the image A before the stimulation.

More specifically, the optimal transformed image is acquired by comparing the image transformed in this manner with the image A by using an appropriate evaluation function.

The registering is performed by calculating the above correlation coefficient γ by using the expression (1) of [Eq. 2] to achieve a transformation that provides the correlation coefficient closest to 1.

In the present invention, the registering method is not limited thereto, but any other known method may be used such as, for example, a method of identifying singular points.

Second Embodiment

Figure 8A:
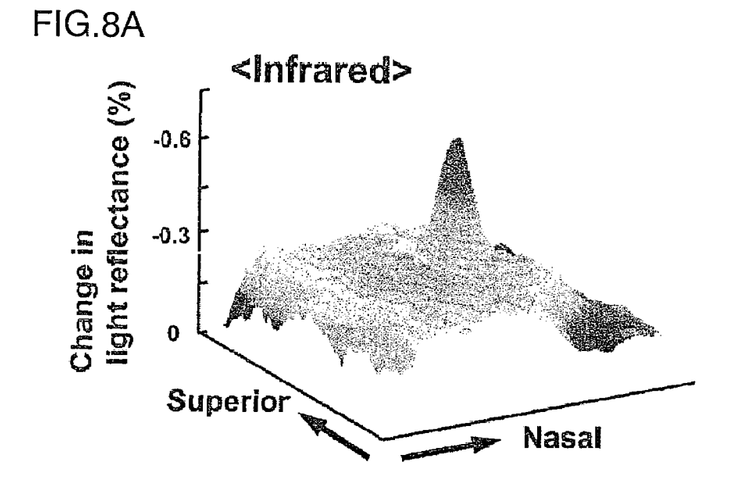
FIGS. 8A, 8B, and 8C are diagrams each showing a second embodiment of the change of the retinal function and the optic disk's function according to the present invention or to the conventional example.
Figure 8B:
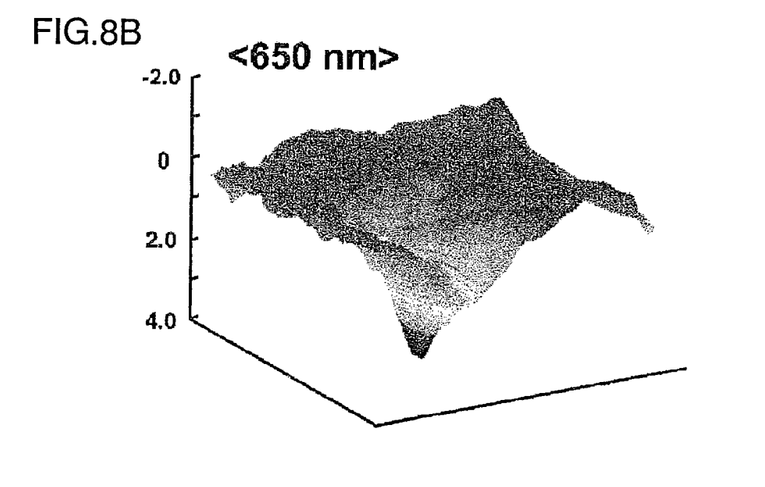
Figure 8C:
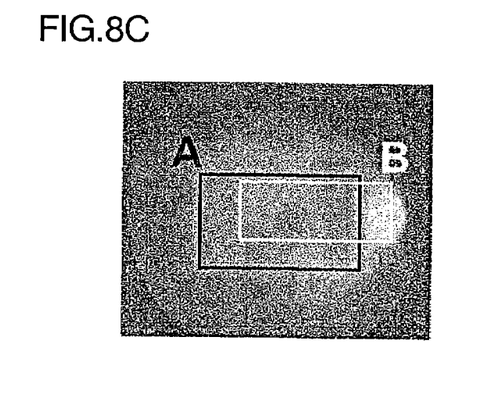

Referring to FIG. 8, there is shown a diagram showing a second embodiment of the change of the retinal function and the optic disk's function according to the present invention and to the conventional example. In this diagram, FIG. 8A shows the embodiment of the present invention, illustrating the change of the retinal function and the optic disk's function of the retinal region enclosed by A in FIG. 8C. FIG. 8B shows an example where a visible light is used for observation and illumination, illustrating the change of the retinal function and the optic disk's function of the retinal region enclosed by B in FIG. 8C.

As shown in FIG. 8B, the example where the visible light is used for the observation and illumination does not genuinely reflect the function of the macular area. Therefore, the discoloration or change in hemoglobin caused by the stimulation is relatively large and it is impossible to detect the change of the intrinsic signal (retinal function) and the optic disk's function. On the other hand, in the present invention, the macular area is illuminated with an infrared light having a wavelength greater than or equal to 800 nm and less than 1000 nm to capture the images. Therefore, it is understood that the measurement is not affected by the discoloration or change in hemoglobin and thus the change of the intrinsic signal genuinely reflecting the photoreceptor function of the macular area is detected accurately.

Third Embodiment

Referring to FIG. 9, there is shown a third embodiment illustrating the change of the retinal function and the optic disk's function according to the present invention. In this diagram, FIGS. 9A, 9B, 9C, and 9D show a fundus photograph of a normal retina, an anatomical distribution chart of cone photoreceptors, a functional topography of the macular area with the optical imaging of the present invention, and a cross-sectional view of FIG. 9C, respectively.

Figure 9A:
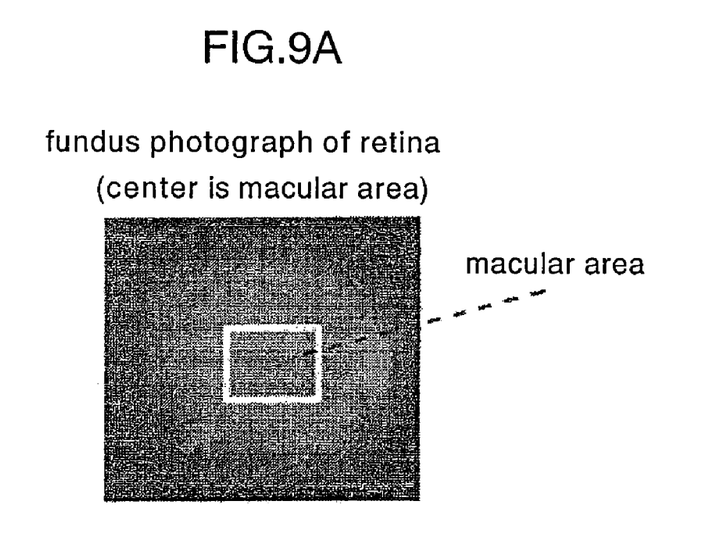
FIGS. 9A, 9B, 9C, and 9D are diagrams showing a third embodiment of the change of the retinal function and the optic disk's function according to the present invention.

In FIG. 9A, the center is the macular area, which is the area having the highest neuron function. The rectangle in this diagram represents the retinal region (recorded area) of the rear surface of the eyeball including the macular area and the optic disk.

Figure 9B:
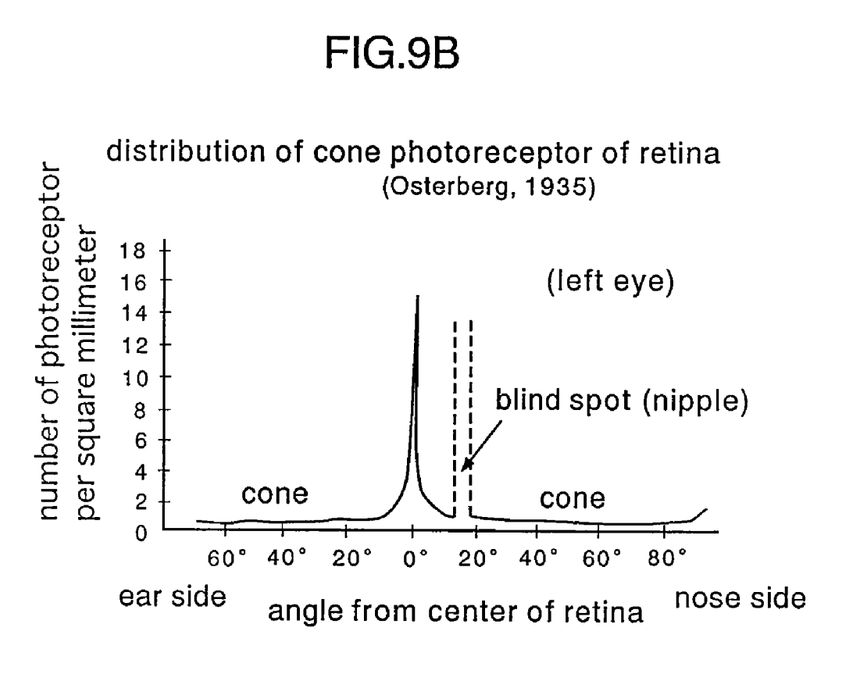

FIG. 9B shows the distribution of cone photoreceptors on the retina, with the abscissa axis representing the angle from the center of the retina and the ordinate axis representing the number of photoreceptors per square millimeter. As apparent from this diagram, the cone photoreceptors important for visual acuity are densely distributed particularly in the macular area.

Figure 9C:
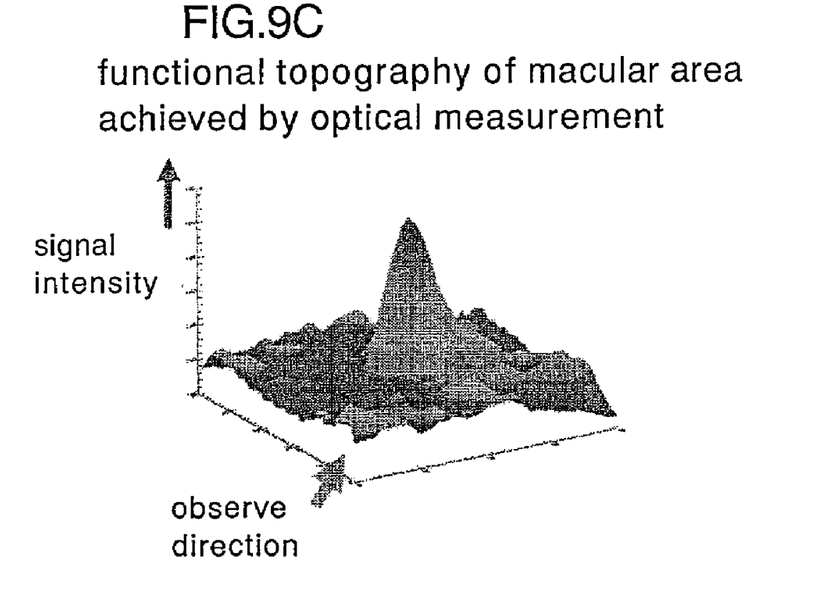
Figure 9D:
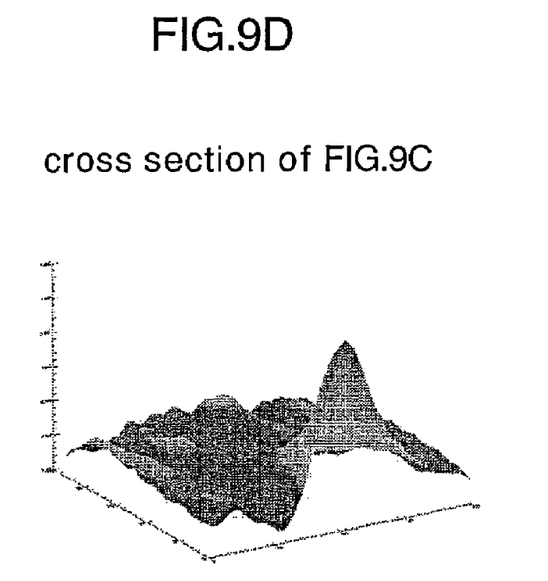

FIGS. 9C and 9D each show a functional topography of the macular area achieved by the optical imaging of the present invention. These diagrams show that there is a peak of the neural activities corresponding to the macular area.

Moreover, it is apparent that the cross section in FIG. 9D highly corresponds to the anatomical distribution shown in FIG. 9B.

Figure 10A:
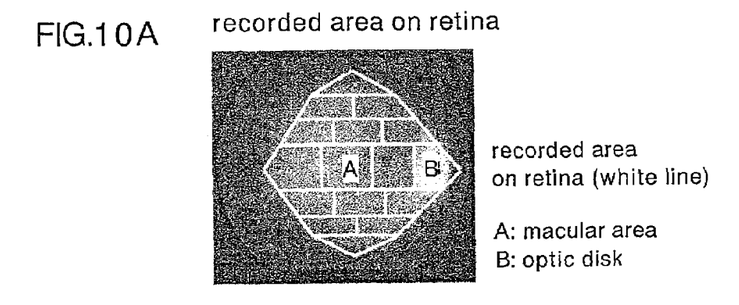
FIGS. 10A, 10B, and 10C are relationship diagrams showing a spatial distribution of neural activities measured by an electroretinogram.
Figure 10B:
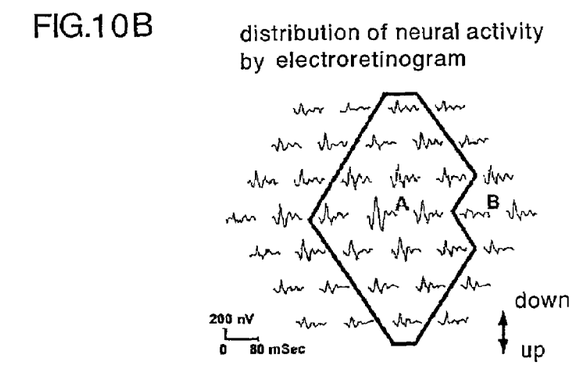

Referring to FIG. 10, there is shown a relationship diagram illustrating the spatial distribution of the neural activities measured by the electroretinograms. In FIG. 10, FIG. 10A shows the retinal region (recorded area) measured by the optical imaging method according to the present invention, which is associated with the recorded area of the electroretinogram in FIG. 10B. Moreover, FIG. 10B shows the electroretinogram for comparing the level of the activity of the area enclosed by the border among the local neural activities (individual waveforms) of the rear surface of the retina with the signal intensity obtained by the optical imaging method according to the present invention in the same area.

Figure 10C:
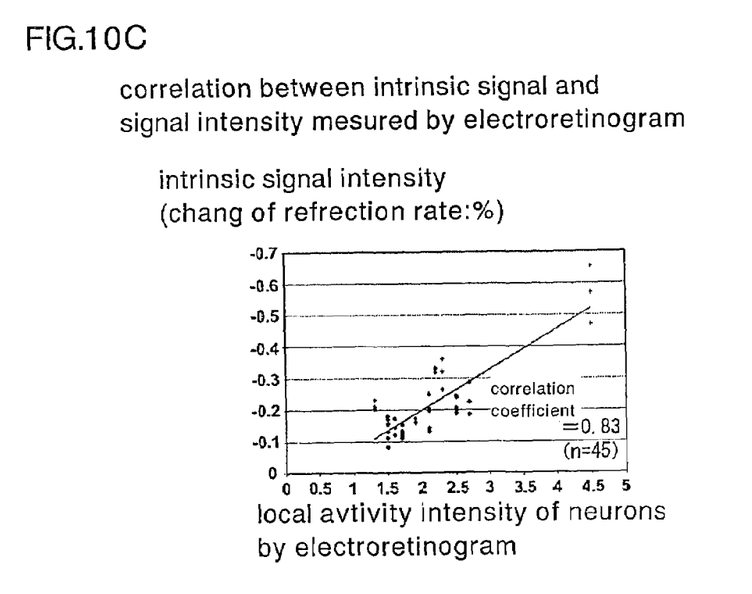

FIG. 10C shows a correlation diagram between the intrinsic signal (the optical imaging method) and the signal intensity measured by the electroretinogram. From this diagram, it is apparent that the signal intensity measured by the optical imaging method of the present invention shows a strong correlation with the electrophysiologic signal intensity measured by the electroretinogram.

As described hereinabove, the method according to the present invention first enables the acquisition of extremely reliable data that compares favorably with data obtained by the conventional method of examination (the record of the electroretinogram).

Moreover, the present invention enables the mapping with the light-adapted cone photoreceptor function and the dark-adapted rod photoreceptor function separated from each other by using the infrared light having a wavelength greater than or equal to 800 nm as an observation light.

Naturally the present invention is not limited to the embodiments described above, but may be varied or modified in various ways without departing from the spirit of the invention.

The invention claimed is:

1. A method for optical imaging of retinal function comprising:
    an illuminating observing step of illuminating the retinal region of the rear surface of an eyeball including the macular area and the optic disk with an invisible light and observing the retinal region;
    a stimulating step of illuminating the retinal region with a visible flash light to stimulate a retinal function including an optic disk's function;
    an imaging step of capturing images A, B before and after the stimulation of the retinal region illuminated with the invisible light; and
    a calculating step of detecting the change of the retinal function of the retinal region from the images A, B before and after the stimulation,
    wherein, in the calculating step, the images A, B before and after the stimulation are registered in advance and the change of the retinal function is displayed with an image from the registered images.

2. The method for optical imaging of retinal function according to claim 1, wherein, in the registering, the image B after the stimulation is subjected to translation, rotation, enlargement or any other linear operation or nonlinear image transformation, the image B' subjected to the linear operation or image transformation is compared with the image A by using an appropriate evaluation function to acquire an optimal image B' registered to the image A.

3. The method for optical imaging of retinal function according to claim 2, wherein the registering is performed by calculating a correlation coefficient γ between the overlapping regions of the two images A and B' or between the corresponding pixel values xi and yi (i is a positive integer) of the feature points by using the expression (1) of [Eq. 1] in order to achieve a transformation that provides the correlation coefficient closest to 1.

[Eq. 1]

$$r = \frac{\sum (x_i - \bar{x})(y_i - \bar{y})}{\sqrt{\sum (x_i - \bar{x})^2} \sqrt{\sum (y_i - \bar{y})^2}} \quad (1)$$

4. The method for optical imaging of retinal function according to claim 2, wherein the image display is performed by calculating a fraction a/b where a and b are the brightness of the image A and the brightness of the image B', respectively, or the difference between them Δ=a−b for each corresponding pixel from the image A before the stimulation and the optimal registered image B' after the stimulation and associating the fraction or the difference with the pixel position on the display.

5. The method for optical imaging of retinal function according to claim 1, wherein:
   the visible flash light is a single or flickering light having a wavelength greater than or equal to 470 nm and less than or equal to 780 nm; and
   the invisible light is an infrared light having a wavelength greater than or equal to 800 nm and less than 1000 nm.

6. An apparatus for optical imaging of retinal function comprising:
   a stimulator for illuminating the retinal region of the rear surface of an eyeball including the macular area with a visible flash light to stimulate a retinal function including an optic disk's function;
   an illuminator for illuminating the retinal region with an invisible light;
   an imaging device for capturing images A, B before and after the stimulation of the retinal region illuminated with the invisible light; and
   a calculator for detecting the change of the retinal function of the retinal region from the images A, B before and after the stimulation,
   wherein the calculator has an image processing program for registering the images A, B before and after the stimulation in advance and subsequently displaying the retinal function with an image from the registered images by using a computer.

7. The apparatus for optical imaging of retinal function according to claim 6, wherein:
   the stimulator is a flash device for emitting a visible flash light having a wavelength greater than or equal to 470 nm and less than or equal to 780 nm in the form of a single or flickering light; and
   the illuminator is an infrared light emitting device for continuously emitting an infrared light having a wavelength greater than or equal to 800 nm and less than 1000 nm.

8. The apparatus for optical imaging of retinal function according to claim 7, further comprising a fixation point forming device for forming a fixation point that can be fixed by an examinee on the retina.

9. The apparatus for optical imaging of retinal function according to claim 8, further comprising an optical filter for selectively dimming a reflected light from the vicinity of the optic disk to capture the images of the macular area without saturation particularly when imaging the function of the retina only.

* * * * *